United States Patent
Zimmermann et al.

(10) Patent No.: US 6,602,472 B1
(45) Date of Patent: Aug. 5, 2003

(54) COUPLING TO MICROSTRUCTURES FOR A LABORATORY MICROCHIP

(75) Inventors: Hans-Peter Zimmermann, Karlsruhe (DE); Gerhard Plé, Karlsruhe (DE)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/570,948

(22) Filed: May 15, 2000

(30) Foreign Application Priority Data

Oct. 1, 1999 (DE) .......................................... 199 47 495

(51) Int. Cl.[7] .................................................. B01L 3/02
(52) U.S. Cl. ........................ 422/100; 422/101; 422/102; 422/103
(58) Field of Search ................................. 422/100, 101, 422/102, 103; 264/34; 216/52; 438/940; 205/701; 435/6; 204/450, 451, 600

(56) References Cited

U.S. PATENT DOCUMENTS

| | | | |
|---|---|---|---|
| 5,658,413 A | | 8/1997 | Kaltenbach et al. |
| 5,744,366 A | * | 4/1998 | Kricka et al. ............... 436/633 |
| 5,993,611 A | * | 11/1999 | Moroney, III et al. ... 204/157.6 |
| 6,033,546 A | * | 3/2000 | Ramsey ...................... 204/603 |
| 6,080,295 A | * | 6/2000 | Parce et al. .................. 204/451 |
| 6,391,622 B1 | * | 5/2002 | Knapp et al. ............ 435/285.2 |

FOREIGN PATENT DOCUMENTS

| | | |
|---|---|---|
| EP | 0638364 A2 | 7/1995 |
| EP | 0897750 A2 | 2/1999 |
| WO | 97/04297 | 2/1997 |
| WO | 97/24604 | 7/1997 |
| WO | 99/03584 | 1/1999 |
| WO | 99/19717 | 4/1999 |
| WO | 99/34920 | 7/1999 |

OTHER PUBLICATIONS

A. Van Den Berg and P. Bergveld, ed. *Micro Total Analysis Systems*. The Netherlands: Kluwer Academic Publishers, 1995. MESA Research Institute monographs, Content overview pp. 1–307.

* cited by examiner

*Primary Examiner*—Jill Warden
*Assistant Examiner*—Brian Sines

(57) ABSTRACT

A laboratory microchip providing a microspray has a substrate having a channel structure on one side thereof. A microspray tip is on the other side of the substrate close to an edge of the substrate. The substrate is deformable in a particular region. Deformation results from thinning the substrate locally in the region or by providing a linear perforation that extends approximately perpendicular to the plane of the substrate. Alternatively, deformation can be obtained by selecting a suitable material for the entire substrate. Substrate deformation can be permanent or reversible.

28 Claims, 5 Drawing Sheets

Figure 1:
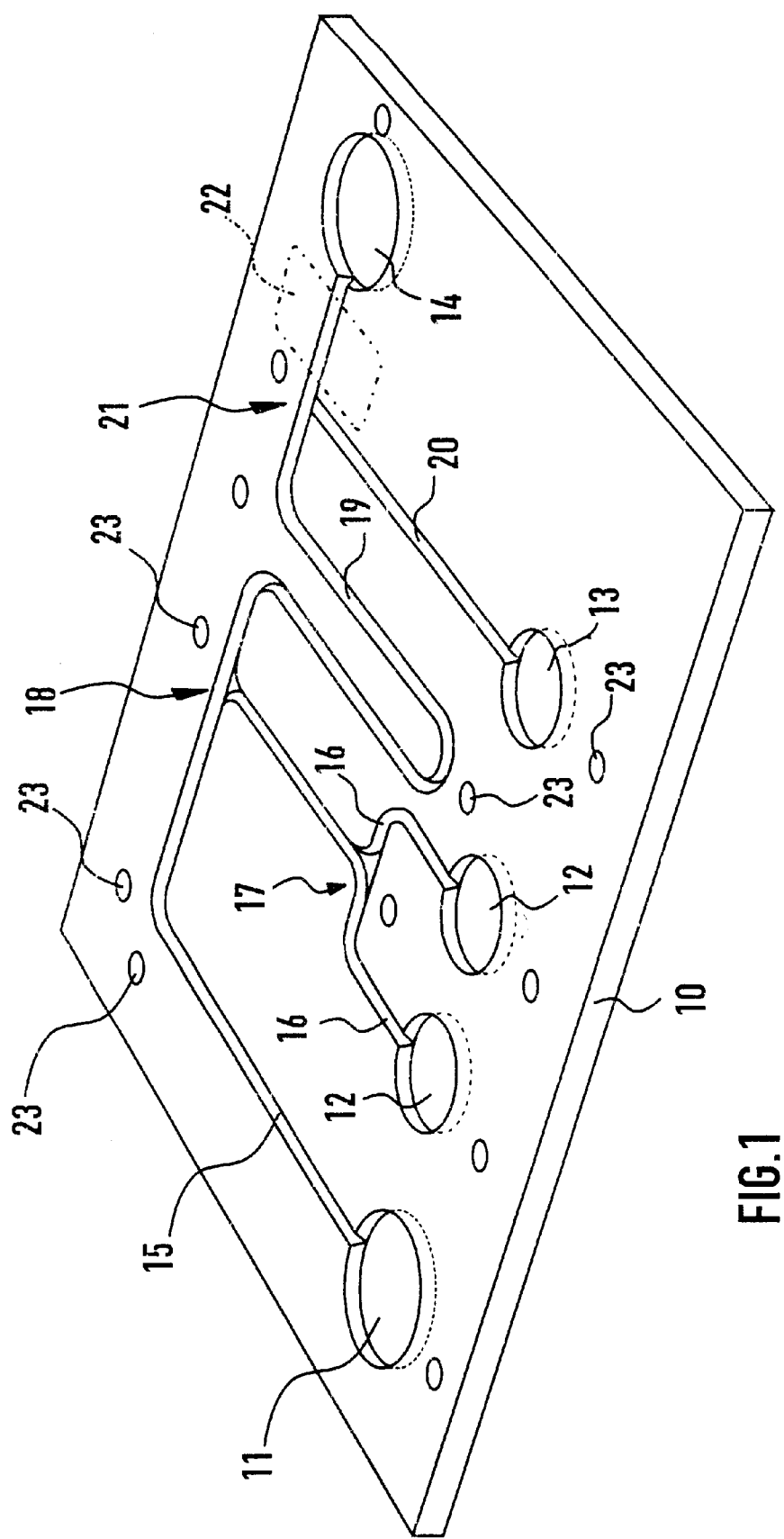

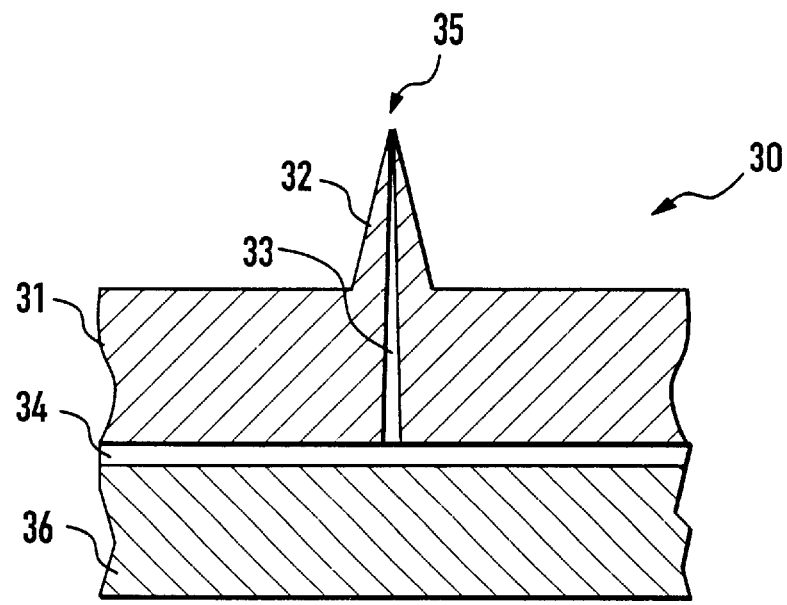
FIG.2
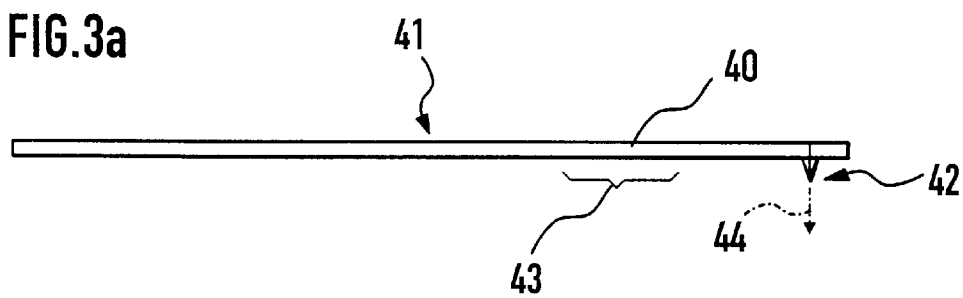
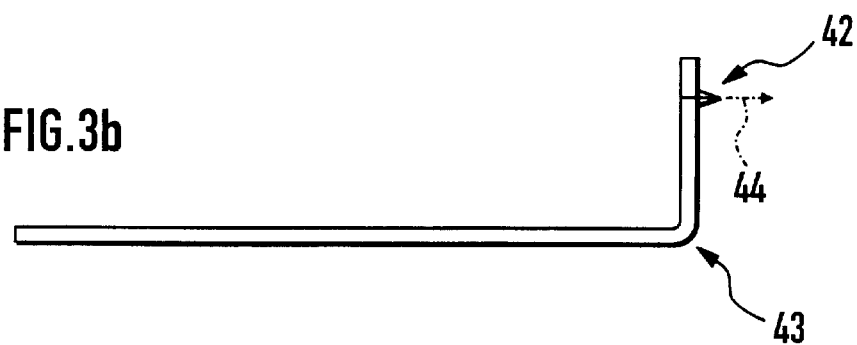

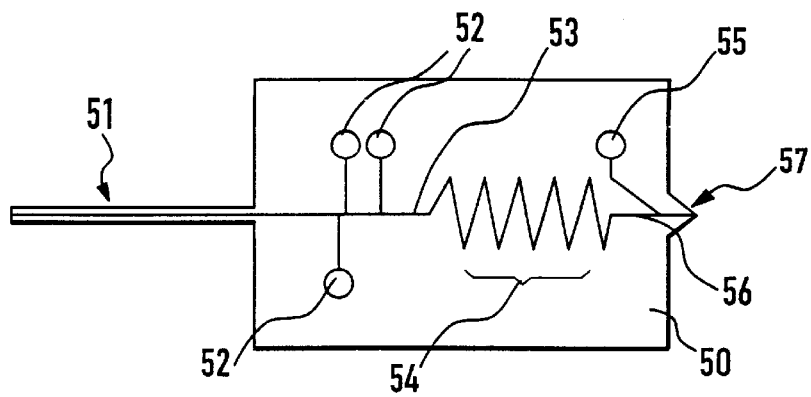
FIG.4a
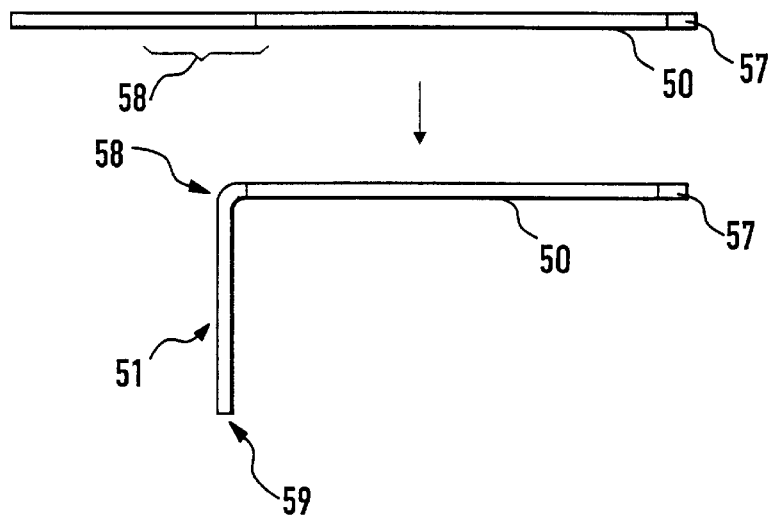
FIG.4b
FIG.4c
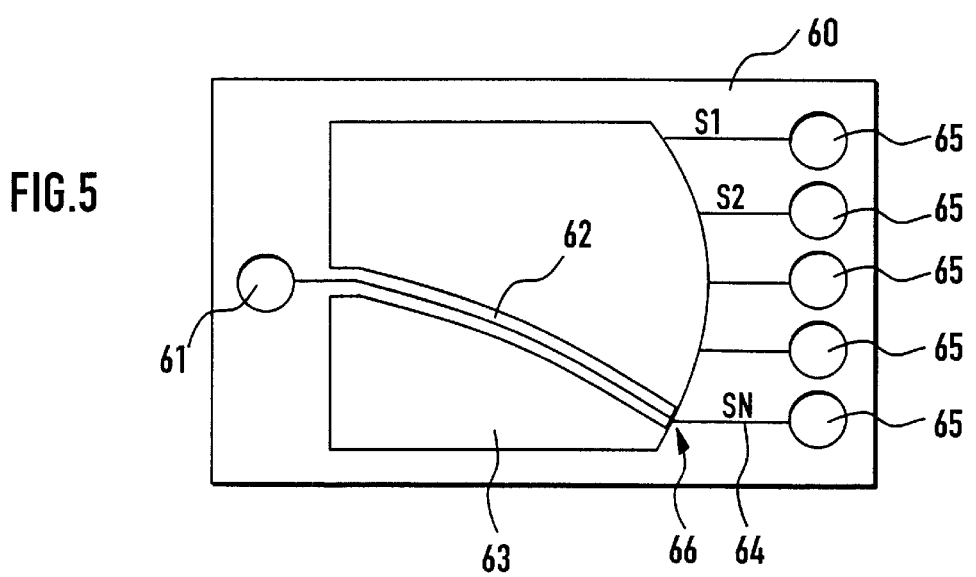
FIG.5

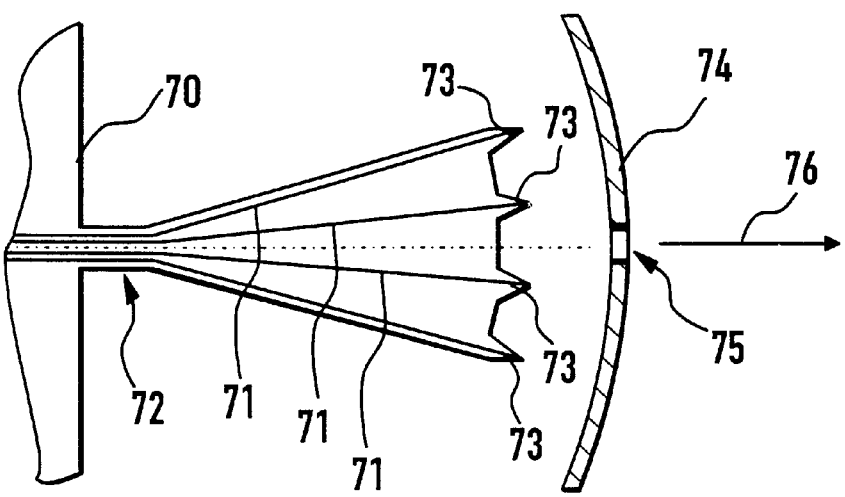
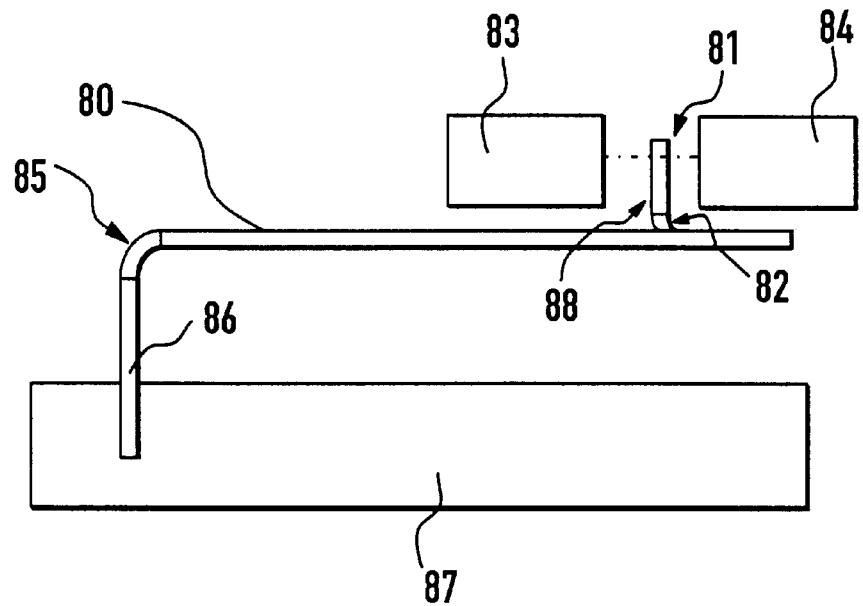

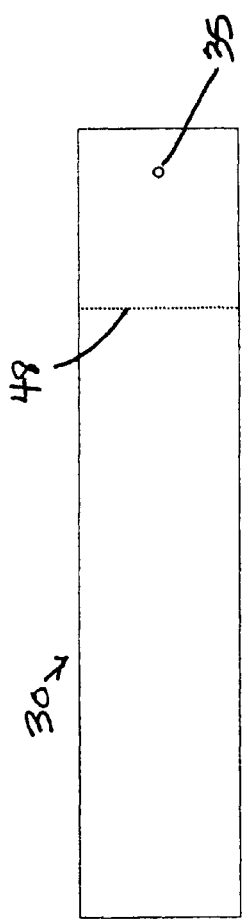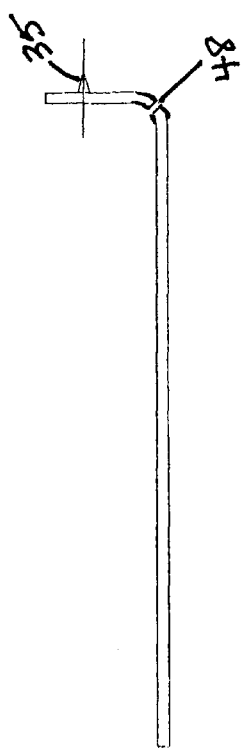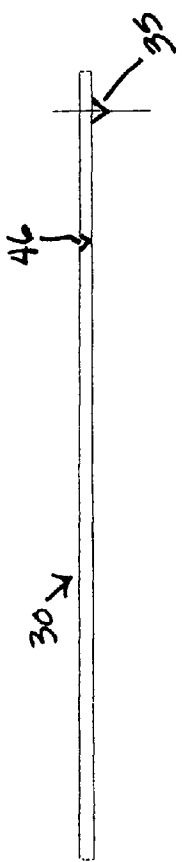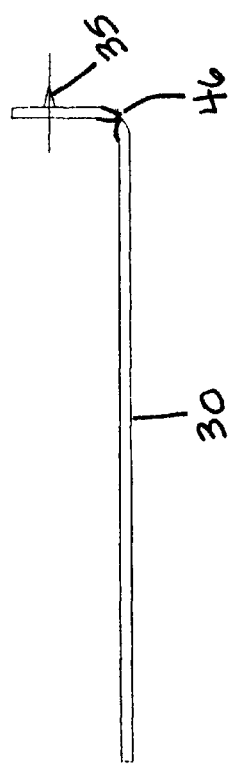

COUPLING TO MICROSTRUCTURES FOR A LABORATORY MICROCHIP

DESCRIPTION

The present invention relates in general to microchip laboratory systems for chemical, physical, and/or biological analysis or synthesis of substances on a substrate having a microfluidics structure. It relates in particular to means of coupling to microstructures for a laboratory microchip of this kind for the purpose of exchanging substances or information between a chip of this kind and the outside world.

The latest developments in the field which is being dealt with here can be compared with equivalent developments in the field of microelectronics. In the fields of chemical analysis and clinical diagnostics too there is a considerable demand for fixed laboratory apparatus to be miniaturised so that it can be built into portable systems. An overview of developments in this area can for example be found in a collection of relevant specialist papers which was edited by A. van den Berg and P. Bergveld under the title "Micrototal Analysis Systems", published by Kluwer Academic Publishers of the Netherlands in 1995. The starting point for these developments were the so-called "capillary electrophoresis" method, which was already established at the time, and efforts which had already been made at earlier stages to implement this method on a planar glass microstructure.

A conventional laboratory microchip of the kind being dealt with here is shown in FIG. 1. In the top face of a substrate 10 are housed microfluidic structures which are used to accommodate and transport substances. The substrate 10 may be formed from glass or silicon for example, and the structures can be produced by a chemical or laser-assisted etching process.

To accommodate the substances to be examined (which will be referred to below as "substance samples") on the microchip, one or more depressions 11 are provided in the substrate which act as reservoirs for the substance sample or samples. To perform an experiment, the sample is first moved along a transport channel 15 in the microchip. In the case of the microchip shown here, the transport channel is formed by a V-shaped groove, although basically it is possible for the transport channel to be of other configurations, e.g. to be a recess or groove of square-cornered or circular shape. In other depressions 12, which also act as reservoirs for substances, are housed any reagents which may be needed to perform an experiment. In the present example these are two different substances which are first fed, via appropriate transport channels 16, to a transport channel junction 17, where they mix and after any chemical analysis or synthesis has taken place form the product which is finally going to be used. Then, in the present example, a further reagent meets the substance sample at a second junction 18, and at this point too the two substances mix. The overall mixture of substances which has been formed in this way then passes through a section of transport channel 19 which, to increase the length of channel traversed, is formed as a meander. In the present example there is yet another reagent contained in another depression 13 designed as a substance reservoir, and this reagent is fed to the mixture of substances which already exists at another junction 21.

Additional depressions 23 provided in the microchip allow electrodes to be fitted to apply a potential which is required to move the substances along the channels. This potential is preferably provided by means of electrical energy and in particular a high voltage. Alternatively, the potential could be generated by means of gas pressure, i.e. hydraulically. Hence, contact is made with the microchip by inserting appropriate electrode tips directly into the depressions 11, 12, 13, 14 intended to hold the substances. By suitably positioning the electrodes 23 along the transport channels 15, 16, 19, 20 and by adjusting the fields applied in the appropriate way in respect of time and/or strength, it is possible to arrange for the movement of the individual substances to take place to an accurately presettable pattern with regard to time and flowrate, thus enabling the kinetics of whatever is the basic reaction process to be allowed for or conformed to with very great accuracy. In cases where the movement of the substances within the microfluidic structure of channels is gas-driven (not shown here), it is necessary for the transport channels to be in the form of fully enclosed ducts, such as hollow passages of circular cross-section. In an embodiment of this kind it is necessary for the depressions 23 to be so formed that suitable pressure-supply ducts enter them at a sealed point so that a pressurising medium, such as an inert gas, can be introduced into the transport passages.

The sensing of the reactions between substances which take place when the particular test or experiment is performed takes place in the present example at a point following on from the junction 21 mentioned, being carried out in a measurement area 22 of the transport channel using a detector which is not shown here. The sensing preferably takes place without any physical contact, and in particular by means of conventional pieces of optical measuring equipment such as optical absorption or fluorescence detectors. The detector required is positioned above or below area 22 in this case. Once the substance has passed through measurement area 22 it is fed to a further depression 14 which acts as a sump for all the waste substances formed in the course of the reaction. Optical detection however calls for optically transparent materials such as glass or polymethyl methacrylate (PMMA), which can in particular be integrated into the substrate of the microchip.

In certain areas of application however, such as protein analysis, optical detection is rather difficult. In such areas it is known for microfluidic microchips to be coupled to a mass spectrometer (MS) by means of a so-called "electrospray interface" (ESI). The particular purpose of the ESI is to ionise the sample, which is present as a liquid phase, for detection by the MS. However, for flowrates of the kind which typically occur in microstructures of the present kind (100–500 nl/min), ESI ionisation requires strong electrical fields of the kind which can only be generated at very fine spray tips with a diameter of 10–100 $\mu$m. Spray tips of this kind can be produced by hot stamping for example. A suitable microspray tip is for example disclosed in a patent application entitled "SPRÜHSPITZE FÜR EINEN MIK-ROFLUIDISCHEN LABOR-MICROCHIP (applicant's reference: DE 2099035) which was filed by the present applicant on the same date as the present document and it will be described in more detail below. However, because of the production process, a spray tip of this kind lies somewhat orthogonally to the plane in which the microchannels described above in the chip are situated.

Where there are sample reservoirs in the microchip and the intention is, by orienting the microchip in three dimensions, to ensure the minimum possible wrong movement of the substances in the channel structure, the chip needs to be held as horizontal as possible. However, with the layout described above, this would mean that ESI substances for interfacing with the MS would have to be sprayed out in the vertical direction. In conventional mass spectrometers however, the infeed or spraying in of substances takes place in the horizontal direction. It is therefore necessary for the direction of spray of substances sprayed out from the microchip to be altered or rotated accordingly.

The supply of substance samples is usually performed by pipetting the substances onto the microchip or by drawing them in by means of a capillary tube bonded onto or into the microchip. For applications where the throughput of samples is high, the samples are preferably fed onto the microchip through a capillary tube, especially to enable the chip to be used for more than one analysis. However, bonding in capillary tubes is a very expensive and complicated business and means that at the transition to the microchip a volume is formed which is generally difficult to flush out.

What is more, the microchip also needs to be held as horizontal as possible to allow the samples to be fed in, to rule out the possibility of any hydrodynamic effects on the movement of the substances in the channel structure. In addition to this, it is useful to avoid any unusable dead volumes when operating the microchip being dealt with here. Particularly in the case of a microchip which has a microspray tip, the access space required for the rest of the operations with the chip will already have been cut down considerably by the spray tip itself, given that on the side which carries the microtip the entire area of the chip substrate will not be accessible or cannot be used to make connections to other supply means, not least because of the fact that the tip is elevated above the substrate.

The object of the present invention is therefore to provide a microchip of the kind described above which does not suffer from the above-mentioned disadvantages and which simplifies microstructural coupling to it, particularly for the exchange of substance samples.

The objects mentioned are achieved in a microfluidic microchip in accordance with the invention in particular by designing the substrate to be deformable at least in a region which contains at least one section of channel. The substrate may in particular be designed to be bendable or foldable locally in this case. The special feature of the invention is that the microstructure of the microchip is designed to be flexible, at least locally, and in particular in a region which contains a part of the channel structure, i.e. a single channel (channel section) or a plurality of channels. By means of the flexible structure it becomes possible for the channel section in question to be bent or folded in three dimensions, as dictated by the particular application, which is an advantage. In this way the direction of spray of a microspray tip which may be present on the microchip can for example be rotated without any reservoirs for substances present on the microchip having to be rotated or tilted at the same time. Hence a change in the direction of spray can advantageously be accomplished simply by bending the microchip locally.

Another possibility which exists is for a suction passage in the form of a "proboscis" to be formed as part of a flexible microstructure of this kind, which passage can in particular be bent down to allow substance samples to be drawn in. This enables substance samples to be fed to the microchip from below without the microchip itself having to be tilted in the process. In particular, the microchip may be horizontally orientated while this is taking place, thus ruling out the possibility of hydrodynamic effects affecting the movement of the substances in the channel structure. At the same time the coupling to the microchip which is obtained in this way is free of dead volumes.

It is also possible for flexible regions of the above kind to be arranged in the interior of the microchip. When this is the case it becomes possible, by using suitable micromechanical elements, to guide substances in quite complex ways, in the way that a substance multiplexer for example does.

The flexible microstructures mentioned can be produced by, in particular, hot stamping, laser ablation or micro injection moulding. The special feature of these processes is that even thin films with a thickness of approximately 10–300 $\mu$m can be structured. In this way it becomes possible to manufacture flexible microstructures which, as dictated by the particular application, can be bent in three dimensions in a similar way to a flexiboard in microelectronics.

By thinning the substrate in a restricted area or producing the entire substrate in a thinned-down form, it becomes possible in these respective cases for it to be bent locally or over its entire area and in this way individual regions of the substrate to be deformed in three dimensions or the whole substrate to be deformed in three dimensions for its entire length. The deformation in this case may be alternatively either permanent or temporary. Where the substrate is deformable temporarily, further means will be required which will stabilise the substrate in whatever state it has been deformed to, at least for the time being. By providing in particular a linear perforation in the substrate, the substrate can be folded in three dimensions along the perforation. Alternatively, the deformable substrate can be formed from a substrate material which is deformable as a whole. This further simplifies the manufacture of the microchip proposed in accordance with the invention and also makes possible more complex deformations, such as simultaneous deformations at a number of points on the microchip.

A microchip according to the invention can advantageously be produced by a two-stage manufacturing process in which a planar substrate is first manufactured, while a channel structure is formed at the same time if required, by using a substrate material which is flexible locally or as a whole, and only then is the substrate which has been produced in this way bent or folded in three dimensions to suit the requirements of the particular application. Alternatively, the manufacturing process provided may be a multi-stage one in which the substrate is first produced in planar form and is then stretched to thin it, or perforated, in a local region or over the entire substrate and only then is bent or folded along the thinned or perforated regions. The microstructures which are also proposed in accordance with the invention, such as a suction proboscis or a comb-like substance transport changeover switch (multiplexer) can advantageously likewise be manufactured in a second stage of manufacture by conventional microstructuring processes.

It is also of advantage for the substrate to be manufactured to be bendable or foldable at least locally in only one direction. This can for example be achieved by producing a micro-perforation of linear form along the axis of rotation or by producing a correspondingly positioned narrow region of thinning in the substrate. The advantage of this arrangement is that it enables the position at which the deformation takes place to be controlled. By means of a linear region of thinning of this kind or a micro-perforation, which acts like a hinge, it becomes possible for example to position a suction tube so that it can be moved around the axis of rotation which has been formed in this way.

Other objects, advantages and features of the microchip according to the invention can be seen from the following description of embodiments.

IN THE DRAWINGS:

FIG. 1 is a perspective view from the side and above a prior art microchip,

FIG. 2 is a sectional view forming an enlargement of part of a laboratory microchip which has a microspray tip, of the kind which is described in, for example, the patent application which is being filed at the same time (applicant's reference: 20-99-0035), FIG. 3 shows a laboratory microchip according to the invention having microspray means, whose direction of spray can be altered, FIG. 4 shows a microchip according to the invention having a sample induction arrangement whose position can be varied, FIG. 5 shows a microchip according to the invention having a micromechanical fraction collector, FIG. 6 shows a microchip according to the invention having a substance transport multiplexer, FIG. 7 shows a microchip according to the invention having an optical detection arrangement working with transmitted light, FIG. 8 is a top view of a microchannel plate with a thinned section prior to the plate being bent, FIG. 9 is a side view of the structure of FIG. 8 after bending, FIG. 10 is a side view of a microchannel plate with microperforations prior to the plate being bent, and FIG. 11 is a side view of the structure of FIG. 10 after bending.

FIG. 1 shows a prior art laboratory microchip and has already been described in detail in the introduction to the specification.

FIG. 2 is a side view in section forming an enlargement of part of a microchip having a microspray tip. The microchip 30 has a substrate 31 on which is arranged a microspray tip 32 which projects approximately perpendicularly from the plane of the substrate. The substrate 31 and spray tip 32 are of monolithic form in this case. Spray tip 32 has a channel 33 passing through it which is used to convey substances to be sprayed from a channel 34 to an opening 35 in the spray tip. Channel 34 is part of a more complex passage structure (not shown) which is sealed off from the outside by a cover plate 36.

FIG. 3 shows an embodiment of a microfluidic microchip according to the invention having a microspray arrangement in which the direction of spray can be varied. A substrate 40 formed as in the embodiment shown in FIG. 1 has a channel structure (not shown) on one side 41. On the other side, in the region of an edge of the substrate, there is a microspray tip 42, which may be formed in the manner shown in FIG. 2 for example.

Substrate 40 is designed to be deformable particularly in a region 43, in which case the deformability may be achieved either by thinning the substrate material locally in this region 43, as illustrated in FIGS. 8 and 9, by thinned section 46, or by means of a linear perforation extending approximately perpendicularly to the plane of the paper, as illustrated in FIGS. 10 and 11 by microperforations 48. Alternatively, the deformability may be obtained by selecting a suitable material for the entire substrate.

A microchip, which has been bent in the manner indicated, is shown in the bottom part of FIG. 3. As can be seen from FIG. 3, the bending of the substrate, which is shown, has turned the direction of spray 44 of microspray tip 42 through 90°. The bending of the substrate may be permanent or reversible in this case. A permanent deformation can be achieved by, for example, selecting a material of a plastic nature for the substrate, whereas a reversible deformation can be achieved by, for example, a material which, in the course of the deformation which is shown here, is still in the plastic stress-strain range. In the case of a reversible deformation, other fixing means (not shown here) are required which make the microchip capable of being immobilised in the bent position.

FIGS. 4a to c show a further embodiment 50 of the microchip according to the invention which has means for sucking in a sample of substance, which means have a bendable drawing-in tube 51. Microchip 50 and drawing-in tube 51 are formed all in one piece in this case, with drawing-in tube 52 being produced from a starting material by a chemical or laser-assisted etching process or else by hot stamping. Microchip 50 also has sample reservoirs 52 each of which opens into a channel 53 which in turn has a substance conveying connection to the drawing-in passage 51. Channel 53 opens in turn into an area of channel 54 which contains a meandering channel structure by means of which the free length of travel for the movement of substances can be artificially lengthened in this area. In the present case, area 54 acts as a separating channel for performing a chemical analysis or synthesis of the substances being handled.

The substances which are finally produced at the end of the separating channel 54 once the chemical analysis or synthesis has taken place are then fed to a microspray tip 57 via a further section of channel 56. Via the spray tip, the substances can then be sprayed into, for example, a mass spectrometer (not shown) which may be coupled to microchip 50. Before the substances are fed into the spray tip, an additional substance which increases or improves the sensitivity of the mass spectrometer examinations to be performed can be fed in from a further substance reservoir 55. Organic acids such as formic or acetic acid to increase the charge (protonisation) of the substances can be fed in in this way. Alternatively, or additionally, organic solvents such as methanol can be fed in to optimise the spraying or atomisation of the substances, in particular by reducing their surface tension.

FIG. 4b is a side view of the microchip shown in FIG. 4a and is in fact a view in the plane of the surface of the microchip. In accordance with the invention the substrate 50 is designed to be deformable in a region 58. As shown in FIG. 3a, the deformability may be achieved in different ways. By bending the drawing-in passage 51 round at the deformable area 58, the state shown in FIG. 4c can then be produced. Here the intake opening of the drawing-in passage points downwards and can thus be dipped into, for example, a conventional substance reservoir (not shown). Due to the "proboscis-like" configuration of the drawing-in passage and the fact that this allows the passage to be bent downwards, the microchip can remain horizontal during a drawing-in process in order to rule out any hydrodynamic effects on the movement of the substances in the channels and passages. At the same time, the present embodiment also has the advantage that the connection to the microchip is free of any dead volumes. What is more, the drawing-in passage can be metallised, which then allows the substance samples to be conveyed out of the particular substance reservoir electro-osmotically.

FIG. 5 shows a further embodiment of microchip in which a chemical or chemico-physical separation of the substances is performed by means of a micromechanical fraction collector. Within a region 63 of the substrate 60, the microchip 60 has a flexible, i.e. bendable, channel the output 66 from which can be conveyed into various channels 64 (S1 to SN). In the course of this the substances are drawn into the particular channels 64 by capillary forces or by hydrodynamic or electro-osmotic forces, i.e. by applying an electrical field between substance reservoir 61 and substances sumps 65. In a refinement of the concept underlying the invention, provision may also be made for the flexible channel 62 to be bendable not (only) in the plane of substrate 60 but also to be bendable so as to project out in a plane perpendicular to the plane of the chip substrate. This will allow substances to be fed into a substance-receiving system positioned above or below the substrate.

FIG. 6 then shows a microchip layout which is suitable for fast detection by means of a mass spectrometer and which can be used in the realm of flight-time spectroscopy for example. With the layout proposed here it becomes possible to operate a detector in such a way that it can be switched between a plurality of separating channels (multiplexed). In an embodiment for this purpose, there are provided in accordance with the invention a plurality of movable microtips 73, of which only one at a time can spray substances through a diaphragm 75 and into a mass spectrometer (not shown), doing so in the direction of arrow 76. The microtips are arranged on a fan-like microstructure 71 which contains channels 71 leading to the individual spraytips. The fan-like structure can be bent sideways at a constriction 72. As in the other embodiments, structure 71 can be positioned on the substrate 70 of a microchip. A microchip of this kind can be manufactured by the manufacturing processes mentioned above.

Finally, FIG. 7 shows a microchip according to the invention for use in an optical detector using transmitted light. A microchip substrate 80 has a tongue-like region 81 which, in the present example, can be bent up at approximately 90°. Provided in region 81 in this case is a so-called detection window 88 which co-operates with an optical measuring arrangement, e.g. an arrangement designed for UV absorption measurement which has a transmitter 83 (a lamp) and a receiver 84 (a photodiode). Transmitter 83 is arranged on one side of window 88 and receiver 84 on the other side of window 88. In accordance with the invention both the transmitter 83 and receiver 84 may in particular be situated on one side, in particular the top side, of microchip substrate 80.

Provided at the other end of substrate 80 is, as in FIG. 3, a drawing-in passage 86 which can be bent down by means of a flexible or deformable region 85 of the substrate. In view of the above-mentioned conditions governing the movement of the substances within the channel structure and also because of the depressions which are provided on the microchip to hold reactant liquids, the microchips have to be used in as nearly horizontal a position as possible, and because of this the microchip can, as shown in FIG. 7, be operated horizontally thanks to the drawing-in passage proposed, in which case the substances to be fed in can be fed to the microchip from below from a substance reservoir 87. The arrangement which is shown for the detection arrangement has the advantage that both the (optical) transmitter and the receiver can be arranged on the same side of the substrate 80 and hence the area below substrate 80 is available for feeding in substances, or in other words there is nothing to interfere physically with this mode of feeding in the substances.

We claim:

1. A microfluidic microchip for chemical, physical, and/or biological analysis or synthesis of substances comprising a deformable substrate carrying a channel structure, the channel structure being arranged so the substances can be moved to follow the channel structure by applying an electrical potential to the channel structure, a portion of the channel structure being on a deformable section of the substrate that is thinner than nondeformable sections of the substrate.

2. A microfluidic microchip for chemical, physical, and/or biological analysis or synthesis of substances comprising a deformable substrate carrying a channel structure, the channel structure being arranged so the substances can be moved to follow the channel structure by applying an electrical potential to the channel structure, a portion of the channel structure being on a deformable section of the substrate that is thinned.

3. A microfluidic microchip for chemical, physical, and/or biological analysis or synthesis of substances comprising a deformable substrate carrying a channel structure, the channel structure being arranged so the substances can be moved to follow the channel structure by applying an electrical potential to the channel structure, a portion of the channel structure being on a deformable section of the substrate that is perforated.

4. A microfluidic microchip for chemical, physical, and/or biological analysis or synthesis of substances comprising a deformable substrate carrying a channel structure, the channel structure being arranged so the substances can be moved to follow the channel structure by applying an electrical potential to the channel structure, a portion of the channel structure being on a deformable section of the substrate that is microperforated.

5. A microfluidic microchip for chemical, physical, and/or biological analysis or synthesis of substances comprising a deformable substrate carrying a channel structure, the channel structure being arranged so the substances can be moved to follow the channel structure by applying an electrical potential to the channel structure, a portion of the channel structure being on a deformable section of the substrate that includes a bendable tubular duct.

6. The microchip of claim 5 wherein the bendable tubular duct includes a suction pipe to draw in substances to be handled.

7. The microchip of claim 5 wherein the duct is metallized along its entire length.

8. A microfluidic microchip for chemical, physical, and/or biological analysis or synthesis of substances comprising a deformable substrate carrying a channel structure, the channel structure being arranged so the substances can be moved to follow the channel structure by applying an electrical potential to the channel structure, a portion of the channel structure being on a deformable section of the substrate that includes a microspray tip having a substance-conveying connection to at least one channel in the channel.

9. The microchip of claim 8 wherein the microspray tip is metallized along its entire length.

10. A microfluidic microchip for chemical, physical, and/or biological analysis of substances comprising a deformable substrate carrying a channel structure, the channel structure being arranged so the substances can be moved to follow the channel structure by applying an electrical potential to the channel structure, a portion of the channel structure being on a deformable section of the substrate, a detector for sensing the presence of the substances in the channel structure, the detector including a radiation source, a radiation receiver and a detection window for passing radiation from the source, the window being between the source and the receiver and on the substrate in the region of one of the channels of the channel structure, and the substances being feedable to the microchip from one side of the substrate by a sample feed-in system, the region of the substrate including the detection window being located on a deformable section of the substrate that can be bent to one side of the substrate so that the radiation source and the radiation receiver on said one side of the substrate are positioned on opposite sides of the detection window, the sample feed-in being arranged so samples can be fed in from the other side of the substrate.

11. The microchip of claim 10, wherein the sample feed-in includes a bendable suction tube.

12. A microfluidic microchip for chemical, physical, and/or biological analysis or synthesis of substances comprising a deformable substrate carrying a channel structure, the channel structure being arranged so the substances can be moved to follow the channel structure by applying an electrical potential to the channel structure, a portion of the channel structure being on a deformable section of the substrate, the substrate including a sprayer coupled with a deformable section of the substrate carrying the channel structure, the sprayer being arranged for spraying the substances away from the substrate into a mass spectrometer, the substrate being deformable in the region of the sprayer so that the orientation in space of the sprayer is variable about at least one axis of rotation.

13. A microfluidic microchip for chemical, physical, and/or biological analysis of substances comprising a deformable substrate carrying a channel structure, the channel structure being arranged so the substances can be moved to follow the channel structure by applying an electrical potential to the channel structure, a portion of the channel structure being on a deformable section of the substrate, first and second sprayers coupled with the channel structure for spraying the substances into an externally positioned detector, the sprayers including at least one diaphragm, the first and second sprayers being movable next to one another relative to the diaphragm.

14. A microfluidic microchip for chemical, physical, and/or biological analysis of an analyte comprising a substrate carrying a channel structure, the channel structure being arranged so the analyte can be moved to follow the channel structure by applying a potential to the channel structure, first and second portions of the channel structure being respectively parts of first and second sections of the substrate, the first section channel structure being at a non-zero angle with respect to the second section channel structure, the first section channel structure being arranged to be responsive to the analyte, the second section channel structure including a segment for delivering a substance to an analyzer of the substance, the substance in the segment including at least part of the analyte, the segment for delivering at least one substance including a spray tip for spraying the substance into the analyzer.

15. The microchip of claim 14 wherein the channel structure of the first section and the segment for delivering are in different planes, the spray tip having an axis in a plane different from the plane of the segment.

16. The microchip of claim 14 wherein the channel structure of the first section and the segment for delivering are in different planes, the spray tip having an axis in the same plane as the plane of the segment.

17. A microfluidic microchip for chemical, physical, and/or biological analysis of an analyte comprising a substrate carrying a channel structure, the channel structure being arranged so the analyte can be moved to follow the channel structure by applying a potential to the channel structure, first and second portions of the channel structure being respectively parts of first and second sections of the substrate, the first section channel structure being at a non-zero angle with respect to the second section channel structure, the first section channel structure being arranged to be responsive to the analyte, the second section channel structure including a segment or delivering a substance to an analyzer of the substance, the substance in the segment including at least part of the analyte, the segment for delivering and the second portion being pivotable relative to a channel segment in the first portion, the channel segment in the first portion being arranged for supplying the analyte to the channel structure of the second portion, wherein the first and second sections are pivotable about a point in a plane including the channel segment in the first portion, the channel segment in the first portion being arranged so the analyte flows past the point, and wherein the second section channel structure includes a plurality of segments for selectively delivering to one substance sump the substance in said channel segment in the first portion, the plurality of segments being pivotable together about the point.

18. The microchip of claim 17 wherein the segment of the second section is arranged for delivering the substance to plural substance sumps locating at different angles with respect to said channel segment in the first portion.

19. The microchip of claim 17 wherein each of the plural segments of the second channel structure includes a spray tip for spraying the substance in the particular segment into the analyzer.

20. A microfluidic microchip for chemical, physical, and/or biological analysis of an analyte comprising a substrate carrying a channel structure, the channel structure being arranged so the analyte can be moved to follow the channel structure by applying a potential to the channel structure, first and second portions of the channel structure being respectively parts of first and second sections of the substrate, the first section channel structure being at a non-zero angle with respect to the second section channel structure, the first section channel structure being arranged to be responsive to the analyte, the second section channel structure including a segment for delivering a substance to an analyzer of the substance, the substance in the segment including at least part of the analyte, the segment in the second section including an optically transparent region between an optical source and an optical detector of the analyzer.

21. The microchip of claim 20 wherein the transparent region is in a plane different from a plane including channel structures of the second portion.

22. A microfluidic microchip for chemical, physical, and/or biological analysis of an analyte comprising a substrate carrying a channel structure, the channel structure being arranged so the analyte can be moved to follow the channel structure by applying a potential to the channel structure, first and second portions of the channel structure being respectively parts of first and second sections of the substrate, the first section channel structure being deformable with respect to the second section channel structure, the first section channel structure being arranged to be responsive to the analyte, the second section channel structure including a segment for delivering a substance to an analyzer of the substance, the substance in the segment including at least part of the analyte, the segment for delivering at least one substance including a spray tip for spraying the substance into the analyzer.

23. The microchip of claim 22 wherein the channel structure of the first section and the segment for delivering are bent so they are in different planes, the spray tip having an axis in a plane different from the plane of the segment.

24. The microchip of claim 22 wherein the channel structure of the first section and the segment for delivering are bent so they are in the same plane as the spray tip having an axis in a plane different from the plane of the segment.

25. A microfluidic microchip for chemical, physical, and/or biological analysis of an analyte comprising a substrate carrying a channel structure, the channel structure being arranged so the analyte can be moved to follow the channel structure by applying a potential to the channel structure, first and second portions of the channel structure being respectively parts of first and second sections of the substrate, the first section channel structure being deformable with respect to the second section channel structure, the first section channel structure being arranged to be responsive to the analyte, the second section channel structure including a segment for delivering a substance to an analyzer of the substance, the substance in the segment including at least part of the analyte, the second section channel structure including a plurality of segments for selectively delivering to one substance sump the substance in said channel segment in the first portion, each of the plural segments of the second channel structure including a spray tip for spraying the substance in the particular segment into the analyzer.

26. A microfluidic microchip for chemical, physical, and/or biological analysis of an analyte comprising a substrate carrying a channel structure, the channel structure being arranged so the analyte can be moved to follow the channel structure by applying a potential to the channel structure, first and second portions of the channel structure being respectively parts of first and second sections of the substrate, the first section channel structure being deformable with respect to the second section channel structure, the first section channel structure-being arranged to be responsive to the analyte, the second section channel structure including a segment for delivering a substance to an analyzer of the substance, the substance in the segment including at least part of the analyte, the segment in the second section including an optically transparent region between an optical source and an optical detector of the analyzer, the transparent region being in a plane different from a plane including channel structures of the second portion.

27. The microchip of claim 26 wherein the potential is electrical.

28. The microchip of claim 26 wherein the potential is fluidic.

* * * * *

UNITED STATES PATENT AND TRADEMARK OFFICE
CERTIFICATE OF CORRECTION

PATENT NO. : 6,602,472 B1
DATED : August 5, 2003
INVENTOR(S) : Hans-Peter Zimmermann and Gerhard Plé

It is certified that error appears in the above-identified patent and that said Letters Patent is hereby corrected as shown below:

Column 8,
Line 52, after "channel" add -- structure --

Column 12,
Line 10, after "structure" delete "-"

Signed and Sealed this

Twenty-first Day of September, 2004

JON W. DUDAS
*Director of the United States Patent and Trademark Office*